United States Patent [19]

Simon

[11] Patent Number: 4,592,443
[45] Date of Patent: Jun. 3, 1986

[54] SOBRIETY INTERLOCK

[76] Inventor: Jack Simon, 7066 Valley Green Cir., Carmel, Calif. 93923

[21] Appl. No.: 571,013

[22] Filed: Jan. 16, 1984

Related U.S. Application Data

[63] Continuation-in-part of Ser. No. 462,815, Feb. 1, 1983.

[51] Int. Cl.$^4$ ............................................. B60K 27/08
[52] U.S. Cl. ........................................ 180/272; 73/23; 340/576
[58] Field of Search ................ 73/23, 27 R; 180/272; 128/719; 340/576

[56] References Cited

U.S. PATENT DOCUMENTS

| | | | |
|---|---|---|---|
| 3,823,382 | 7/1974 | Gaddy | 180/272 X |
| 3,830,630 | 8/1974 | Kiefer et al. | 128/719 X |
| 3,831,707 | 8/1974 | Takeuchi | 180/272 |
| 3,855,573 | 12/1974 | Honda et al. | 180/272 X |
| 4,039,852 | 8/1977 | Miyamoto et al. | 128/719 X |
| 4,093,945 | 6/1978 | Collier et al. | 180/272 |
| 4,132,109 | 1/1979 | Vander Syde | 73/23 |
| 4,314,564 | 2/1982 | Albarda | 73/23 X |

FOREIGN PATENT DOCUMENTS

| | | | |
|---|---|---|---|
| 2327823 | 12/1974 | Fed. Rep. of Germany | 180/272 |
| 52938 | 4/1980 | Japan | 180/272 |

Primary Examiner—David M. Mitchell
Assistant Examiner—Michael Mar
Attorney, Agent, or Firm—Townsend and Townsend

[57] ABSTRACT

Apparatus for detecting alcohol on the breath including a microprocessor programmed to test breath temperature to guard against circumvention of the test. When the temperature test is passed, the breath alcohol concentration is measured. Responsive to the alcohol concentration, the microprocessor either: enables the ignition for a sober driver; enables the ignition for a tipsy but not drunk driver; disables the ignition, and imposes a programmed wait before allowing the test to be attempted again.

27 Claims, 9 Drawing Figures

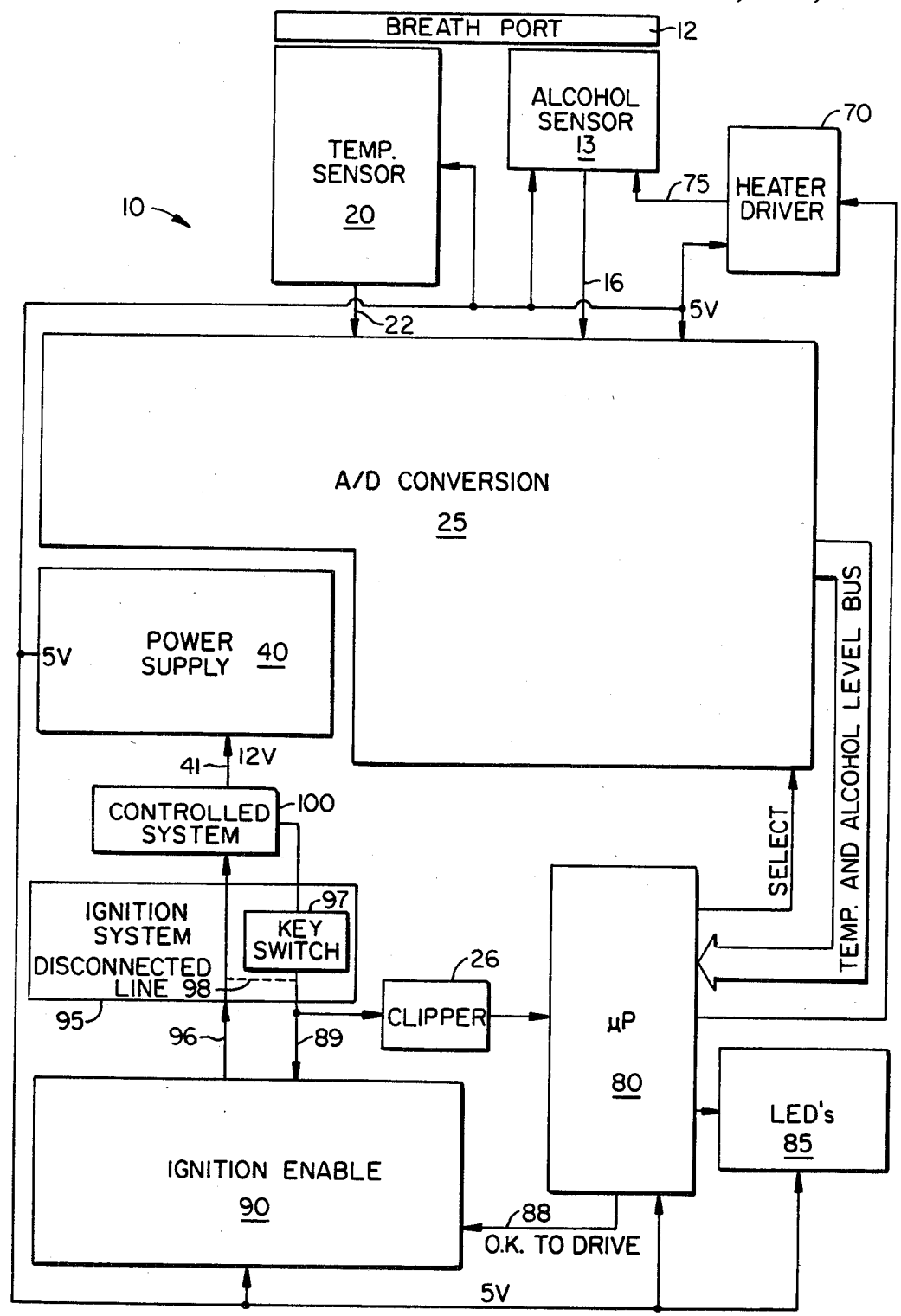
FIG._1.

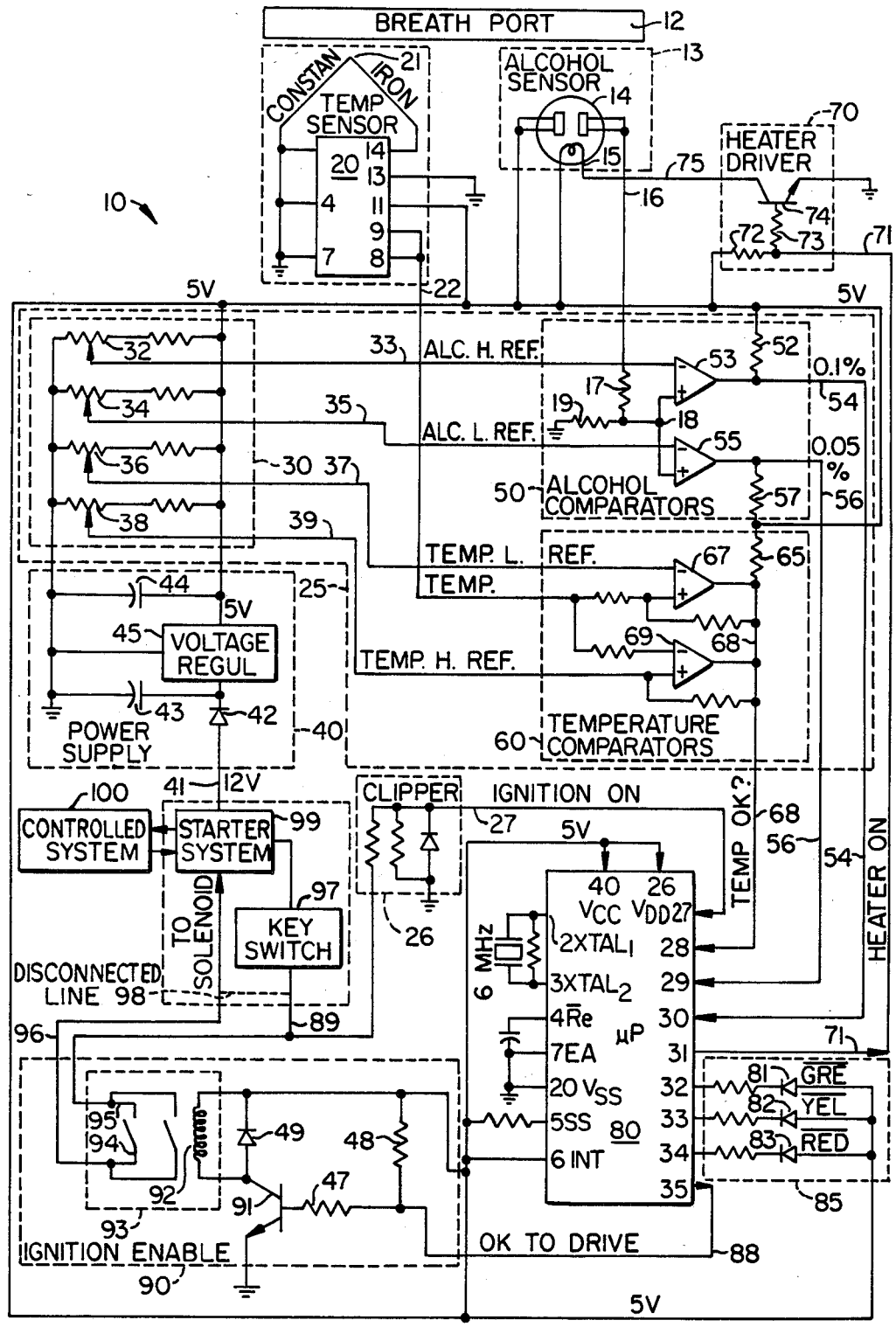
FIG._2.

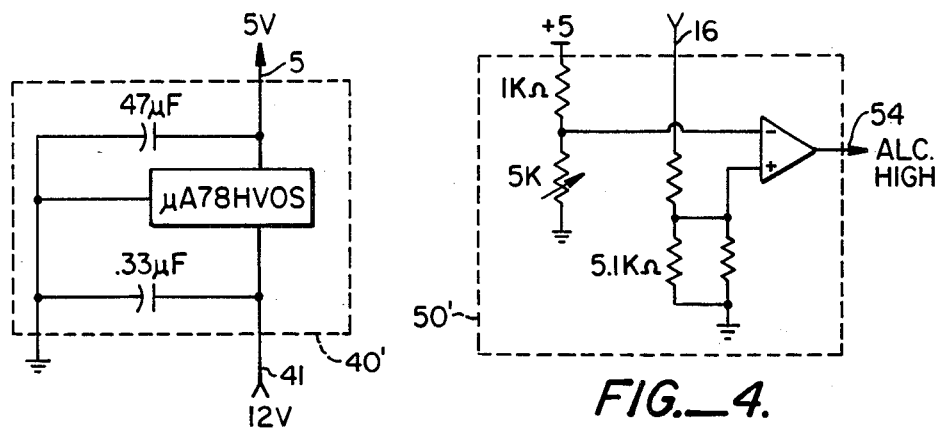
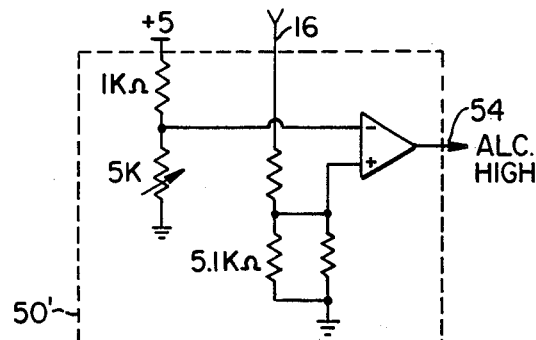
FIG._3.
FIG._4.
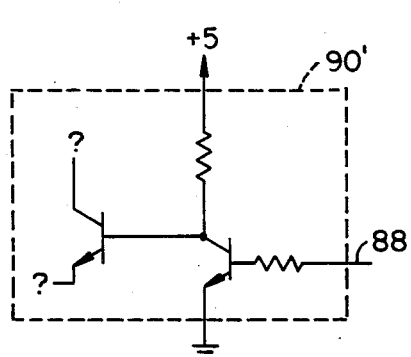
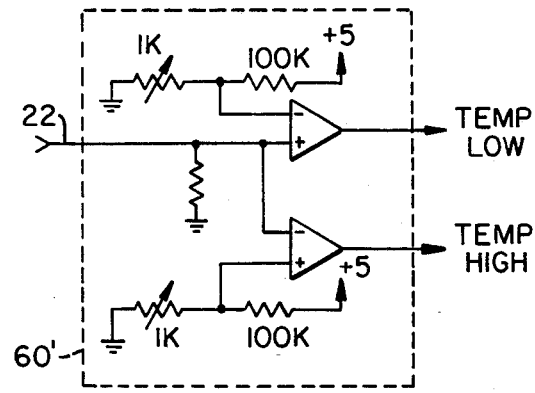
FIG._5.
FIG._6.
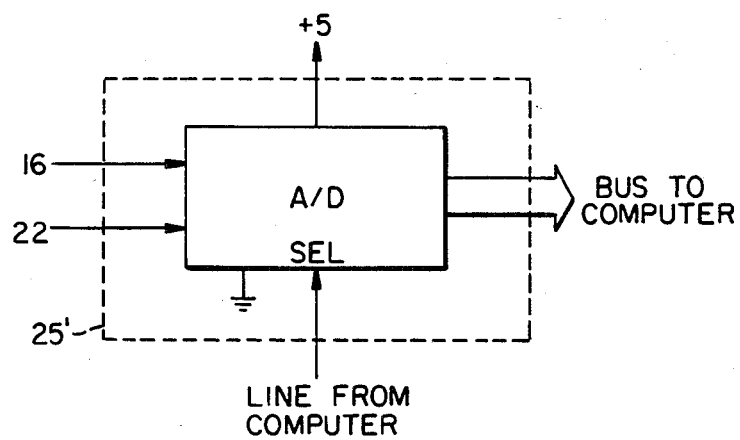
FIG._7.

SOBRIETY INTERLOCK

This is a continuation-in-part application of application Ser. No. 462,815, filed Feb. 1, 1983.

BACKGROUND OF THE INVENTION

1. Field of the Invention

The present invention relates to alcohol testing devices and specifically to a device which uses the results of a sobriety breath test to control a switch in an automobile ignition system or in other machinery.

2. Description of the Prior Art

Automobile driving by intoxicated persons is a serious problem responsible for thousands of accidental deaths and extensive property damage every year, yet despite various preventive efforts the problem has defied solution. Many schemes have been suggested to prevent drunks from driving, but because the schemes have all involved some driver inconvenience, none has gained widespread acceptance. Alcohol intoxication can be detected in various ways, all suffering from some drawback. A practical preventive test must be executed automatically without supervision.

Reaction time and dexterity test results such as disclosed in U.S. Pat. Nos. 3,665,447 and 3,610,943 respectively depend on individual abilities, are only indirectly related to degree of intoxication, and are not always meaningful. Alcohol intoxication is directly measured in a driver's breath by U.S. Pat. No. 3,186,508 by measuring the optical property change of a chemical solution which is bleached by reacting with alcohol fumes. This system requires an inconvenient frequent change of the solution. U.S. Pat. No. 3,823,382 tests intoxication directly by an exothermic reaction of chemical granules with alcohol in a breath sample with a mercury thermostat to measure the amount of heat generated. The thermostat must be replaced after a failed test. U.S. Pat. No. 4,093,945, tests intoxication by oxidizing any alcohol in a breath sample and measures the heat given off by a change in the electrical resistance of a sensor. That system is relatively complex and expensive.

In short, prior art drunk-driving prevention devices generally can be evaded, are inaccurate, unreliable, tedious, inconvenient, or complex and prohibitively expensive. For these and other reasons, no drunk-driving prevention system has gained wide-spread acceptance. There remains, therefore, a real need for a convenient, reliable, and inexpensive sobriety interlock system.

SUMMARY OF THE INVENTION

It is the principal object of this invention to provide an improved sobriety interlock which takes advantage of a microprocessor to achieve convenient, reliable, and economical control over operation of automobiles or other machinery by inebriated persons. The microprocessor is programmed to make more flexible and advantageous use of breath sensors than was previously known. The interlock requires only a simple connection to an electrical starter system and derives its power from the starter system. No chemicals are used and routine replacement of material is not required. The microprocessor first tests breath temperature, using a thermocouple, to guard against circumvention of the test. When the temperature test is passed, the breath alcohol concentration is measured based on the balance between adsorption and desorption of ethanol at the surface of a semiconductor sensor. The balance causes a measurable resistance change.

Responsive to the alcohol concentration, the microprocessor either: activates a steady green light and enables the ignition for a sober driver; activates a blinking yellow light and enables the ignition for a tipsy but not drunk driver; or activates a steady red light, disables the ignition, and imposes a programmed wait before allowing the test to be attempted again. The test may be repeated, after waiting each time until passed.

BRIEF DESCRIPTION OF THE DRAWINGS

FIG. 1 is a block diagram of the sobriety interlock 10 used with a controlled system 100;

FIG. 2 is a preferred embodiment of the invention showing details of circuits that may be used for the blocks in FIG. 1;

FIGS. 3, 4, 5, 6, and 7 are examples of alternative circuits that may be used for the blocks in FIG. 1;

DETAILED DESCRIPTION OF THE PREFERRED EMBODIMENT

Figure 8:
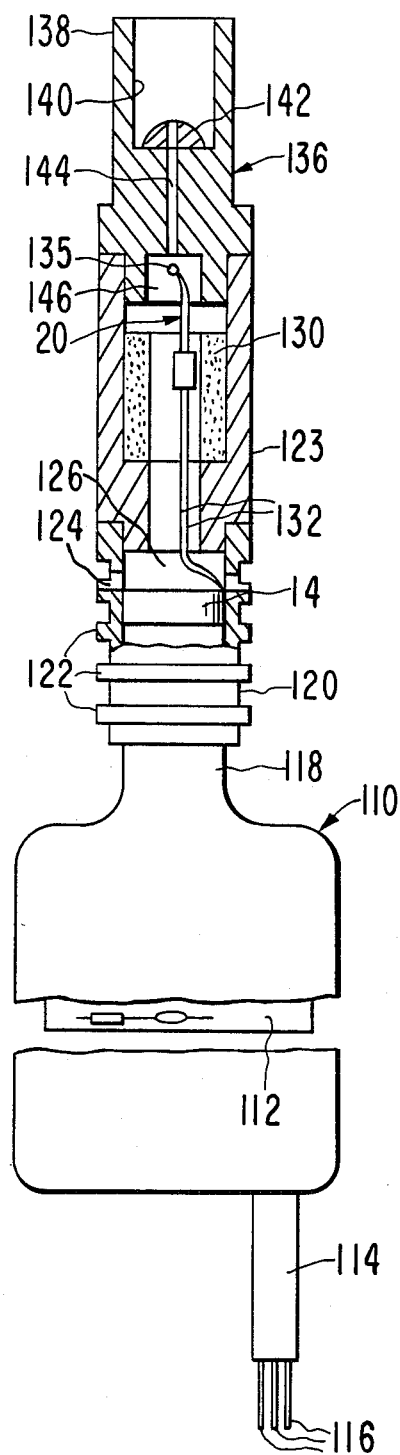
FIG. 8 is a side elevational view, partly broken away and in section, of the sobriety interlock, showing the mouthpiece attached to a housing containing the electronic circuitry of the invention.

The present invention, a sobriety interlock 10, may be inserted as in FIG. 1 into a system controller, to test a human operator for sobriety and to prevent system use until the test has been passed. For example, the invention may be used in the ignition system 78 (FIG. 2) of an automobile, or in other machinery that should not be operated by intoxicated persons. The sobriety interlock is installed in an automobile 100 by disconnecting line 98 between the key switch 97 and the solenoid in the starter system 99. The ends of disconnected line 98 are reconnected to the input 89 and to the output 96 of an ignition enable circuit 90 controlled by microprocessor 80 (FIGS. 1 and 2), preferably Intel Model No. 8048. The interlock uses five volt power line 5 supplied by power supply 40 which is connected directly to the 12 volt car battery, not shown, allowing the interlock to operate regardless of whether key switch 97 is closed. In low temperatures, contaminants gradually adsorb into, and bias the characteristics of, sensor 14 (FIG. 2), which is preferably Model No. TGS 812 made by the Figaro Engineering Co. Continuous standby activation of heater coil 15 (FIG. 2) by heater driver 70 keeps alcohol sensor 14 free of contamination.

One begins the sobriety test by turning the key in ignition switch 97. Referring to FIG. 2, the current in line 89 passes through clipper 26 which clips spikes and smooths the voltage level to produce an "ignition on" signal on line 27. "Ignition on" signal 27 resets processor 80 and starts it on a routine such as the program in Appendix A, which works with an Intel 8048 as processor 80. First, a "heater on" signal is applied through line 71 to driver circuit 70 for several minutes to heat coil 15 and sensor 14 from standby to ready condition. Computer 80 may activate heater driver 70 by a 12 volt supply from line 41 alternated with, or instead of, 5 volt line 5 in order to heat sensor 14 faster. During the heat-up period, computer 80 blinks the three LEDs 85 in rotation. Each LED preferably has its cathode connected through a 220 ohm resistor to a computer I/O pin, and its anode connected to the 5 volt supply. Even when free of previous contamination, the sensitivity of alcohol sensor 14 is affected by temperature.

Heater coil 15 maintains the sensor at a known constant temperature to minimize the effect of ambient air temperature. Heater 15 is turned off by a low voltage on driver 70, which pulls the base of transistor 74 low and prevents it from turning on the transistor. A high voltage on driver 70 provides sufficient current through resistor 73 and the base and emitter of transistor 74 for the transistor to conduct current to its grounded emitter from collector line 75, heater coil 15, and 5 volt supply 5 (or 12 volt supply 41). If alcohol sensor output line 16 were connected directly (not shown) to one of the computer input pins, the computer could measure the voltage drop across semiconductor sensor 14 to determine its resistance and thereby its temperature, indicating whether the sensor is ready.

When the sensor is heated and ready for a test, green LED 81 lights steadily. The prospective driver then breathes into port 12. To guard against circumvention of the sobriety interlock, a breath temperature sensor 20, preferably a type J monolithic thermocouple amplifier model AD594 by the Analog Devices Co., is used to measure the air temperature in breath port 12. Temperature sensor 20 varies the voltage on line 22 according to the (breath) temperature at point 21 in breath port 12. To determine whether the temperature in port 12 is within a ±5° F. range around normal 98° F. human breath temperature, the line 22 test voltage is compared by temperature comparators 60 against a temperature floor reference 37 and a ceiling reference 39. The temperature references may be supplied through adjustable 5K ohm resistors 36 and 38 in a reference voltage supply circuit 30.

Floor reference voltage 37, representing 95° F., is applied to the negative input terminal of comparator 67, and ceiling voltage 39, representing 105° F., is applied to the positive input of comparator 69. The temperature test voltage 22 is applied through respective resistors 23 and 24, both preferably 12K ohms, to the positive input of floor comparator 67, and to the negative input of comparator 69. Temperature voltages 22 above the floor and below the ceiling cause both comparators 67 and 69 to act as sources of current flowing out through resistor 65, preferably 9.1K ohms, to supply voltage line 5. This results in greater than 5 volts on "Temp OK?" line 68, which acts as a "wired AND" gate providing input to pin C28 of computer 80. Although the temperature indication voltage on line 22 will always satisfy at least one of the comparisons and that comparator will raise the voltage on line 68, if the line 22 voltage does not also satisfy the other comparison, that other comparator will act as a sink and pull the line 68 voltage below the signal threshold of computer input pin C29. When "Temp OK" line 68 has remained high for the programmed number of seconds, LED display 85 changes from steady green to all three blinking in unison while the alcohol level is tested for about 1.5 seconds.

Rather than using comparators 50 and 60, voltage reference supply 30, and their output lines, A-D converter 25 may be used to supply digitized values of temperature 22 and alcohol 16. Computer 80 is thus self-calibrating and would then compare against values stored internally.

The proportion of alcohol present in the breath is measured by gas sensor 13. Sensor 13 includes a tin dioxide semiconductor 14 whose resistance is changed by absorption and desorption of ethanol according to the gaseous concentration at the sensor surface (as well as the resistance being changed by temperature). The sensor output voltage on line 16 indicates the ethanol concentration. Current flowing to ground through resistors 17 and 19, preferably 1.5K ohms and 6.8K ohms respectively, reduces the voltage from line 16 to a lower voltage in line 18.

Empirical tests have determined that the breath of a person having a blood alcohol level of 0.05% (tipsy, but not considered legally impaired) will cause the sensor 14 to produce 3.1 volts on line 18. Testing a person having a 0.10% blood alcohol level will produce 1.9 volts on line 18. Reference voltage supply circuit 30 provides alcohol reference voltages 33 and 35, equal to these levels, derived through variable resistors 32 and 34 by which the references may be calibrated. Comparator 55 compares the alcohol level voltage on line 18 against the 0.05% (lower) standard on line 35, and produces a current in its output line 56 through resistor 57 according to the outcome of the comparison. An alcohol level less than low reference 35 causes comparator 55 to act as a current sink, reducing the voltage in line 56 to less than 5 volts. Conversely, a test result voltage 18 greater than low reference 35 causes comparator 55 to act as a current source raising the voltage in line 56 above 5 volts.

Comparator 53 operates similarly to cause a current through preferably 9.2K ohm resistor 52 and produce less than 5 volts in line 54 for alcohol test results less than the high reference in line 33, and more than 5 volts in line 54 for test results greater than reference line 33.

Microprocessor 80 uses the temperature verification signal 68 and the alcohol level comparison results 54 and 56 to decide whether the sobriety test has been passed. An alcohol level below 0.05% activates the green LED continuously, and a high voltage "OK to Drive" signal output on line 88 preferably through a 1K ohm resistor 47. A high signal on line 88 to the base of transistor 91, preferably a 2N4401, and preferably current from the 5 volt supply through a 10K ohm resistor 48, cause the transistor to conduct current through its collector and a coil 92 in relay 93, preferably an AROMAT HBZE. Current flowing in coil 92 creates a magnetic field which attracts arms 94 towards contacts 95, completing the circuit around disconnected line 98.

A blood alcohol level between 0.05% and 0.10% provides a "tipsy" flashing yellow LED 82 which means that the vehicle should be driven with caution. A high "OK to Drive" signal enables relay 93.

If the blood alcohol level is above 0.10%, the breath test is failed and interlock 10 will not allow the car 100 to be started. "OK to Drive" line 88 is held low, and red LED 83 blinks. The key switch 97 must be turned off and back on again to bring computer 80 to a "power up" condition and to restart the test. A four minute "long warm up" must be endured while heater 15 clears the sensor and hopefully the kidneys clear the blood, of alcohol contamination.

Figure 9:
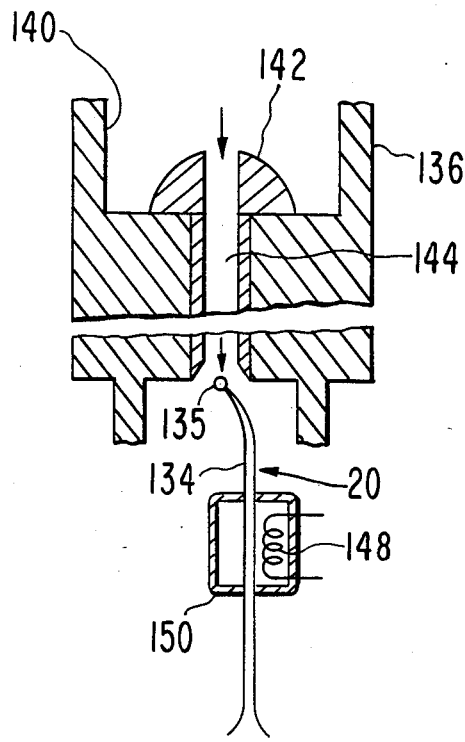
FIG. 9 is a view similar to FIG. 8 but enlarged to show the placement of a thermocouple relative to a breath port or orifice.

A preferred embodiment of the structure defining the mouthpiece and the support for the electronic circuitry of sobriety interlock 10 is shown in FIGS. 8 and 9. This structure includes a housing 110 which is of a suitable material, such as rigid plastic, and which is rugged in construction. The housing is provided to contain and to protect the circuit boards and other electronic components contained therewithin against damage, such as in the event that the housing is dropped on a surface. One of the circuit boards 112 is shown in FIG. 8 within housing 110. A cable 114 having leads 116 extending outwardly therefrom connects the electronic circuitry with an external power source, such as the battery of a vehicle, and also connects the circuitry with the ignition system of the vehicle.

Housing 110 has a tubular neck 118 to which a tubular extension 120 is secured. Member 120 is rigid and can be formed from any suitable material, such as aluminum. For purposes of illustration, extension 120 includes a metallic member 121; such as of aluminum and a rigid plastic member 123 secured to and extending outwardly from one end of member 121. The outer surface of member 121 has annular ribs 122 thereon to help in dissipating heat absorbed in the member.

Sensor 14 is mounted in any suitable manner, such as by a press fit within member 121 near the outer open end thereof. Gas sensor 14 is adjacent to a number of spaced openings 124 through member 121 so that the space 126 adjacent to the outer face of gas sensor 14 communicates with the atmosphere to assist in cleaning the sensor as hereinafter described.

Member 123 contains a tubular, heat insulating element 130 typically of cork for shielding a portion of the breath temperature sensor 20 which is coupled by leads 132 to the circuitry in housing 110, leads 132 extending through member 120 as do a pair of leads (not shown) coupled with gas sensor 14. Such leads are connected to the circuitry contained in housing 110. Temperature sensor 20 includes a thermocouple 134 shown in more detail in FIG. 9.

A mouthpiece member 136 is secured to the outer end of member 123 and has an outer end 138 over which the mouth is placed for blowing a breath sample into mouthpiece member 136. An internal bore 140 in mouthpiece 136 contains a tubular element 142 having a fluid flow passage 144 therethrough, whereby the breath sample under pressure in bore 140 can enter the space 146 containing thermocouple 134.

Thermocouple 134 is shown in its preferred location in FIG. 9 at the downstream end of passage 144. It can be seen from FIG. 9 that the thermocouple junction 135 is physically at the end of passage 144. The reason for this is that the thermocouple will be immediately sensitive to the temperature of the breath before the breath expands into space 146 and is thereby cooled.

Thermocouple 134 has a heating element 148 in heat exchange relationship thereto at a location spaced a short distance, such as 0.25 to 0.50 inch, from junction 135 as shown in FIG. 9. Heater 148 comprises a heating coil within a vacuum envelope 150 surrounding a portion of thermocouple 134. The purpose of heating coil 148 is to eliminate the tendency for sobriety interlock 10 to automatically turn itself on if the ambient temperature was about 98° F. To eliminate this problem, the heater 148 is placed in heat exchange relationship to the thermocouple, specifically to both wires thereof, to heat the thermocouple to a temperature above the 98° normal breath temperature. For example, it can be heated to 130° F. and this is controlled by microprocessor 80 so that the temperature of the heated portion of the thermocouple remains at about 130° F. A small transistor can be switched on and off to regulate and stay at this temperature level, this heating being done by conduction to the junction 135 of the thermocouple. Thus, when a person blows into mouthpiece member 136 with the breath temperature at about 98° F., the thermocouple cools down from the 130° F. temperature so that sobriety interlock 10 can then commence a valid test.

Another important feature of the structure shown in FIGS. 8 and 9 is the use of passage 144 which typically has a diameter of 0.075" to 0.130". Thus, passage 144, which provides, in effect, a small orifice, forces a person to blow into the mouthpiece such that a slight air pressure is developed in the mouthpiece member. This forces the lips of the person to maintain an air seal about the mouthpiece member so as to prevent outside air from entering the breath sample directed into and through passage 144. Outside air would otherwise alter the results of the operation of sobriety interlock 10.

Passage 144, because it has a finite length, directs the breath flow onto the thermocouple junction 135 and then through extension 120 and onto gas sensor 14. To do this, a temperature of 95° F. must be sensed by the thermocouple for a period of at least four seconds so that a deep lung breath sample is measured. Since openings 124 (FIG. 8) are provided in member 121, the gas sensor will be in free air which is essential for cleanup of the sensor. With the use of openings 124, it is possible to conduct a first test and have the sensor cleaned up in order to make a next test in less than 15 seconds.

Another feature of the present invention with respect to the cleanup of gas sensor 14 involves the use of a frequency (about 10 to 100 Hz) controlled voltage source applied to the sensor during the cleanup period. This frequency controlled voltage source is used instead of a steady voltage source to heat the sensor. Ordinarily, with a steady voltage, the cleanup period is about ten seconds as recommended by the manufacturer of the gas sensor. By using a frequency controlled, variable voltage source generated by microprocessor 80 to heat the sensor, this cleanup time is cut to less than five seconds. It is also possible to improve the accuracy of the gas sensor results. This is done by using the microprocessor 80 to check the level at which gas sensor 14 is cleaned up to, at the time a test is started. This starting point has a significant bearing on the results of an alcohol breath test. In the analog to digital version of sobriety interlock 10, compensation for any variation to starting point can be adjusted automatically by the microprocessor 80.

Details have been disclosed to illustrate the invention in a preferred embodiment of which adaptions and modifications within the spirit and scope of the invention will occur to those skilled in the art. The scope of the invention is limited only by the following claims.

The program can also contain in software an option such that, if a vehicle is not operated for 48 hours or other time period, the automatic cleaning cycle for the gas sensor is overridden to prevent the drain on the battery of the vehicle which supplies power to the circuitry. Thus, the circuit shuts itself off. The only disadvantage of this is that cleaning of the gas sensor may take a minute when the vehicle is next operated rather than 10 seconds for normal operation.

A control program for use with interlock 10 is shown on the following pages.

SOBERLIZER CONTROL PROGRAM

REGISTER USAGE

REGISTER BANK ZERO

```
    7       6       5       4       3       2       1.      0
+-----------------------------------------------------------------+
|           COUNTER USED BY LONGWARMUP AND GRACEWAIT              |
+-----------------------------------------------------------------+
|                                                                 |
+-----------------------------------------------------------------+
|              UTILITY COUNTER USED BY PURGE, ETC                 |
+-----------------------------------------------------------------+
|      COUNTER FOR "WAIT 1 SEC BUT ABORT IGN ON/OFF" ROUTINES     |
+-----------------------------------------------------------------+
|              USED TO SAVE A DURING CLOCK INTERRUPT              |
+-----------------------------------------------------------------+
|                 OUTPUT VALUE TO SEND TO P1                      |
+-----------------------------------------------------------------+
|                 OUTPUT VALUE TO SEND TO P2                      |
+-----------------------------------------------------------------+
|ALC>.10|ALC>.05|          |ALC10  |ALC05  |TEMPOK |IGN ON |
|       BREATH TEST RESULTS         |       INPUT STATUS         |
+-----------------------------------------------------------------+
```

REGISTER BANK ONE

```
    7       6       5       4       3       2       1       0
+-----------------------------------------------------------------+
| RED   |YELLOW | GREEN | RED   |YELLOW | GREEN | CYCLE | BLINK |
| BASIC LED PATTERN     | CURRENT LED PATTERN   | LED ACTIVITY  |
+-----------------------------------------------------------------+
|          DOWN COUNTER USED BY "TICK" TO CONTROL LED TIMING      |
+-----------------------------------------------------------------+
|                                                                 |
+-----------------------------------------------------------------+
|                                                                 |
+-----------------------------------------------------------------+
|                                                                 |
+-----------------------------------------------------------------+
|                  COUNTER USED BY "WAIT .01 SEC"                 |
+-----------------------------------------------------------------+
|                  COUNTER USED BY "WAIT .01 SEC"                 |
+-----------------------------------------------------------------+
|                  COUNTER USED BY "WAIT 1 SEC"                   |
+-----------------------------------------------------------------+
```

| ADDRESS | INSTR | | SOURCE | COMMENTS |
|---------|-------|----------|--------|----------|
| 300 | E5 | POWERON: | SEL MB0 | POWER ON COMES HERE |
| 301 | 04 | | JMP POWERUP | |
| 302 | 20 | | | |
| 303 | 93 | | RETR | DUMMY INTERRUPT SERVER |
| | | | | |
| 007 | 64 | | JMP TICK | CLOCK TICK SERVER |
| 008 | 40 | | | |
| | | | | |
| 020 | E5 | POWERUP: | SEL MB0 | |
| 021 | C5 | | SEL RB0 | |
| 022 | BD | | MOV R5,#0F | |
| 023 | 0F | | | |
| 024 | BE | | MOV R6,#00 | |
| 025 | 00 | | | |
| 026 | BF | | MOV R7,#00 | |
| 027 | 00 | | | |
| 028 | 23 | | MOV A,#7D | |
| 029 | 7D | | | |
| 02A | 62 | | MOV T,A | |
| 02B | 55 | | STRT T | |
| 02C | 25 | | EN TCNTI | |
| 02D | 00 | | NOP | |
| 02E | 00 | | NOP | |
| 02F | 00 | | NOP | |
| 030 | 54 | LONGWARMUP: | CALL SETLCYCLE | START LEDS CYCLING |
| 031 | 00 | | | |
| 032 | 54 | | CALL HEATON | TURN ON HEATER |
| 033 | 10 | | | |
| 034 | B8 | | MOV R0,#F0 | START 4 MINUTE TIMEOUT |
| 035 | F0 | | | |
| 036 | 74 | LWU1: | CALL WAIT1SEC | WAIT 1 SECOND |
| 037 | 00 | | | |
| 038 | E8 | | DJNZ R0,LWU1 | LOOP TILL 4 MINUTES UP |
| 039 | 36 | | | |
| 03A | 00 | | NOP | |
| 03B | 00 | | NOP | |
| 03C | 00 | | NOP | |
| 03D | 00 | | NOP | |
| 03E | 00 | | NOP | |
| 03F | 00 | | NOP | |
| 040 | 54 | IGNOFF: | CALL SETLCYCLE | START LEDS CYCLING |
| 041 | 00 | | | |
| 042 | BD | | MOV R5,#EF | |
| 043 | EF | | | |
| 044 | BE | | MOV R6,#00 | |
| 045 | 00 | | | |
| 046 | 54 | | CALL PURGE | |
| 047 | 40 | | | |
| 048 | 00 | | NOP | |
| 049 | 00 | | NOP | |
| 04A | FF | | MOV A,R7 | |
| 04B | 12 | | JB0 IGNON | |
| 04C | 60 | | | |
| 04D | 04 | | JMP IGNOFF | |
| 04E | 40 | | | |
| 04F | 00 | | NOP | |
| | | | | |
| 060 | 14 | IGNON: | CALL SHORTWARMUP | |
| 061 | D0 | | | |
| 062 | 54 | | CALL BLINKGRN | |
| 063 | 08 | | | |

| ADDRESS | INSTR | | SOURCE | COMMENTS |
|---------|-------|---|--------|----------|
| 064 | 00 | | NOP | |
| 065 | 00 | | NOP | |
| 066 | 34 | | CALL TESTBREATH | |
| 067 | 00 | | | |
| 068 | 00 | | NOP | |
| 069 | 00 | | NOP | |
| 06A | FF | | MOV A,R7 | |
| 06B | F2 | | JB7 DRUNK | |
| 06C | A0 | | | |
| 06D | D2 | | JB6 TIPSY | |
| 06E | 78 | | | |
| 06F | 00 | | NOP | |
| 070 | 00 | SOBER: | NOP | |
| 071 | 00 | | NOP | |
| 072 | 54 | | CALL STEADYGRN | |
| 073 | 28 | | | |
| 074 | 00 | | NOP | |
| 075 | 00 | | NOP | |
| 076 | 04 | | JMP DRIVE | |
| 077 | 80 | | | |
| 078 | 00 | TIPSY: | NOP | |
| 079 | 00 | | NOP | |
| 07A | 54 | | CALL BLINKYEL | |
| 07B | 30 | | | |
| 07C | 00 | | NOP | |
| 07D | 00 | | NOP | |
| 07E | 00 | | NOP | |
| 07F | 00 | | NOP | |
| 080 | 54 | DRIVE: | CALL HEATOFF | |
| 081 | 18 | | | |
| 082 | FE | | MOV A,R6 | |
| 083 | 43 | | ORL A,#10 | |
| 084 | 10 | | | |
| 085 | AE | | MOV R6,A | |
| 086 | 00 | WAITIGNOFF: | NOP | |
| 087 | 00 | | NOP | |
| 088 | FF | | MOV A,R7 | |
| 089 | 12 | | JB0 WAITIGNOFF | |
| 08A | 86 | | | |
| 08B | 04 | | JMP GRACE | |
| 08C | B0 | | | |
| | | | | |
| 0A0 | 00 | DRUNK: | NOP | |
| 0A1 | 00 | | NOP | |
| 0A2 | 54 | | CALL BLINKRED | |
| 0A3 | 38 | | | |
| 0A4 | FF | DRUNK1: | MOV A,R7 | |
| 0A5 | 12 | | JB0 DRUNK1 | |
| 0A6 | A4 | | | |
| 0A7 | BA | | MOV R2,#0A | |
| 0A8 | 0A | | | |
| 0A9 | EA | | DJNZ R2,* | |
| 0AA | A9 | | | |
| 0AB | 04 | | JMP LONGWARMUP | |
| 0AC | 30 | | | |
| | | | | |
| 0B0 | FE | GRACE: | MOV A,R6 | DISABLE STARTER |
| 0B1 | 53 | | ANL A,#EF | |
| 0B2 | EF | | | |
| 0B3 | AE | | MOV R6,A | |
| 0B4 | 54 | | CALL HEATON | |
| 0B5 | 10 | | | |
| 0B6 | B8 | | MOV R0,#F0 | 4-MINUTE GRACE PERIOD |

| ADDRESS | INSTR | | SOURCE | COMMENTS |
|---------|-------|---|--------|----------|
| 0B7 | F0 | | | |
| 0B8 | 74 | GRACEWAIT: | CALL W1SBAION - *music waiting* | |
| 0B9 | 30 | | | |
| 0BA | FF | | MOV A,R7 | |
| 0BB | 12 | | JB0 DRIVE | IF IGN ON, GO START CAR |
| 0BC | 80 | | | |
| 0BD | E8 | | DJNZ R0,GRACEWAIT | |
| 0BE | B8 | | | |
| 0BF | 04 | | JMP IGNOFF | |
| 0C0 | 40 | | | |
| | | | | |
| 0D0 | 54 | SHORTWARMUP: | CALL HEATON | |
| 0D1 | 10 | | | |
| 0D2 | B8 | | MOV R0,#20 | |
| 0D3 | 20 | | | |
| 0D4 | FF | SWULOOP: | MOV A,R7 | |
| 0D5 | 37 | | CPL A | |
| 0D6 | 12 | | JB0 SWUEXIT | |
| 0D7 | DC | | | |
| 0D8 | 74 | | CALL W1SBAIO | |
| 0D9 | 20 | | | |
| 0DA | E8 | | DJNZ R0,SWULOOP | |
| 0DB | D4 | | | |
| 0DC | 83 | SWUEXIT: | RET | |
| | | | | |
| 100 | 00 | TESTBREATH: | NOP | |
| 101 | 00 | | NOP | |
| 102 | 00 | | NOP | |
| 103 | 00 | | NOP | |
| 104 | FF | | MOV A,R7 | |
| 105 | 53 | | ANL A,#0F | |
| 106 | 0F | | | |
| 107 | AF | | MOV R7,A | |
| 108 | 00 | | NOP | |
| 109 | 00 | | NOP | |
| 10A | BA | WAITSTABLE: | MOV R2,#32 | |
| 10B | 32 | | | |
| 10C | FF | WSLOOP: | MOV A,R7 | |
| 10D | 37 | | CPL A | |
| 10E | 12 | | JB0 TBEXIT | |
| 10F | 32 | | | |
| 110 | 32 | | JB1 WAITSTABLE | |
| 111 | 0A | | | |
| 112 | 74 | | CALL WAIT01 | |
| 113 | 10 | | | |
| 114 | EA | | DJNZ R2,WSLOOP | |
| 115 | 0C | | | |
| 116 | 00 | | NOP | |
| 117 | 00 | | NOP | |
| 118 | BA | | MOV R2,#96 | START ALCOHOL TEST |
| 119 | 96 | | | |
| 11A | FF | ALCLOOP: | MOV A,R7 | |
| 11B | 37 | | CPL A | |
| 11C | 12 | | JB0 TBEXIT | |
| 11D | 32 | | | |
| 11E | 32 | | JB1 WAITSTABLE | |
| 11F | 0A | | | |
| 120 | 00 | | NOP | |
| 121 | 00 | | NOP | |
| 122 | 37 | | CPL A | |
| 123 | 53 | | ANL A,#0C | |

| ADDRESS | INSTR | | SOURCE | COMMENTS |
|---------|-------|---|--------|----------|
| 124 | 0C | | | |
| 125 | 47 | | SWAP A | |
| 126 | 4F | | ORL A,R7 | |
| 127 | AF | | MOV R7,A | |
| 128 | 00 | | NOP | |
| 129 | 00 | | NOP | |
| 12A | 74 | | CALL WAIT01 | |
| 12B | 10 | | | |
| 12C | EA | | DJNZ R2,ALCLOOP | |
| 12D | 1A | | | |
| 12E | 00 | | NOP | |
| 12F | 00 | | NOP | |
| 130 | 00 | | NOP | |
| 131 | 00 | | NOP | |
| 132 | 34 | TBRET: | CALL BLINKALL | |
| 133 | F8 | | | |
| 134 | 74 | | CALL W1SBAIO | |
| 135 | 20 | | | |
| 136 | 74 | | CALL W1SBAIO | |
| 137 | 20 | | | |
| 138 | 00 | | NOP | |
| 139 | 00 | | NOP | |
| 13A | 83 | | RET | |
| | | | | |
| 1F8 | D5 | BLINKALL: | SEL RB1 | |
| 1F9 | B8 | | MOV R0,#FD | |
| 1FA | FD | | | |
| 1FB | C5 | | SEL RB0 | |
| 1FC | 83 | | RET | |
| | | | | |
| 200 | D5 | SETLCYCLE: | SEL RB1 | |
| 201 | B8 | | MOV R0,#26 | |
| 202 | 26 | | | |
| 203 | B9 | | MOV R1,#01 | |
| 204 | 01 | | | |
| 205 | C5 | | SEL RB0 | |
| 206 | 83 | | RET | |
| | | | | |
| 208 | D5 | BLINKGRN: | SEL RB1 | |
| 209 | B8 | | MOV R0,#25 | |
| 20A | 25 | | | |
| 20B | C5 | | SEL RB0 | |
| 20C | 83 | | RET | |
| | | | | |
| 210 | FD | HEATON: | MOV A,R5 | |
| 211 | 43 | | ORL A,#10 | |
| 212 | 10 | | | |
| 213 | AD | | MOV R5,A | |
| 214 | 83 | | RET | |
| | | | | |
| 218 | FD | HEATOFF: | MOV A,R5 | |
| 219 | 53 | | ANL A,#EF | |
| 21A | EF | | | |
| 21B | AD | | MOV R5,A | |
| 21C | 83 | | RET | |
| | | | | |
| 220 | D5 | LEDSOFF: | SEL RB1 | |
| 221 | B8 | | MOV R0,#0 | |
| 222 | 00 | | | |
| 223 | C5 | | SEL RB0 | |
| 224 | 83 | | RET | |

| ADDRESS | INSTR | | SOURCE | COMMENTS |
|---|---|---|---|---|
| 228 | D5 | STEADYGRN: | SEL RB1 | |
| 229 | B8 | | MOV R0,#24 | |
| 22A | 24 | | | |
| 22B | C5 | | SEL RB0 | |
| 22C | 83 | | RET | |
| | | | | |
| 230 | D5 | BLINKYEL: | SEL RB1 | |
| 231 | B8 | | MOV R0,#49 | |
| 232 | 49 | | | |
| 233 | C5 | | SEL RB0 | |
| 234 | 83 | | RET | |
| | | | | |
| 238 | D5 | BLINKRED: | SEL RB1 | |
| 239 | B8 | | MOV R0,#91 | |
| 23A | 91 | | | |
| 23B | C5 | | SEL RB0 | |
| 23C | 83 | | RET | |
| | | | | |
| 240 | 00 | PURGE: | NOP | |
| 241 | 00 | | NOP | |
| 242 | 54 | | CALL HEATON | |
| 243 | 10 | | | |
| 244 | B8 | | MOV R0,#05 | CYCLE 5 SECONDS ON |
| 245 | 05 | | | |
| 246 | FF | PONLOOP: | MOV A,R7 | |
| 247 | 12 | | JB0 PURGEXIT | |
| 248 | 58 | | | |
| 249 | 74 | | CALL W1SBAION | |
| 24A | 30 | | | |
| 24B | E8 | | DJNZ R0,PONLOOP | |
| 24C | 46 | | | |
| 24D | 54 | | CALL HEATOFF | |
| 24E | 18 | | | |
| 24F | B8 | | MOV R0,#F0 | |
| 250 | F0 | | | |
| 251 | FF | POFFLOOP: | MOV A,R7 | |
| 252 | 12 | | JB0 PURGEXIT | |
| 253 | 58 | | | |
| 254 | 74 | | CALL W1SBAION | |
| 255 | 30 | | | |
| 256 | E8 | | DJNZ R0,POFFLOOP | |
| 257 | 51 | | | |
| 258 | 83 | PURGEXIT: | RET | |
| | | | | |
| 300 | D5 | WAIT1SEC: | SEL RB1 | |
| 301 | BF | | MOV R7,#64 | |
| 302 | 64 | | | |
| 303 | C5 | | SEL RB0 | |
| 304 | 74 | W1SECLOOP: | CALL WAIT01SEC | |
| 305 | 10 | | | |
| 306 | D5 | | SEL RB1 | |
| 307 | EF | | DJNZ R7,W1SECLOOP | |
| 308 | 04 | | | |
| 309 | C5 | | SEL RB0 | |
| 30A | 83 | | RET | |
| | | | | |
| 310 | D5 | WAIT01SEC: | SEL RB1 | |
| 311 | BE | | MOV R6,#08 | |
| 312 | 08 | | | |
| 313 | BD | W01SECLOOP: | MOV R5,#FA | |

```
ADDRESS  INSTR              SOURCE                  COMMENTS
------   -----              ------                  --------

314      FA                 |
315      ED                 DJNZ R5,*
316      15                 |
317      EE                 DJNZ R6,W01SECLOOP
318      13                 |
319      C5                 SEL RB0
31A      83                 RET 320      00     W1SBAI0:    NOP
321      00                 NOP
322      BB                 MOV R3,#64
323      64                 |
324      74     W1SBAI0LP:  CALL WAIT01SEC
325      10                 |
326      FF                 MOV A,R7
327      37                 CPL A
328      12                 JB0 W1SBAI0RET
329      2C                 |
32A      EB                 DJNZ R3,W1SBAI0LP
32B      24                 |
32C      83     W1SBAI0RET: RET 330      00     W1SBAION:   NOP
331      00                 NOP
332      BB                 MOV R3,#64
333      64                 |
334      74     W1SBAIONLP: CALL WAIT01SEC
335      10                 |
336      FF                 MOV A,R7
337      00                 NOP
338      12                 JB0 W1SBAIONRET
339      3C                 |
33A      EB                 DJNZ R3,W1SBAIONLP
33B      34                 |
33C      83     W1SBAIONRET: RET

340      C5     TICK:       SEL RB0
341      AC                 MOV R4,A
342      FF                 MOV A,R7
343      53                 ANL A,#F0
344      F0                 |
345      AF                 MOV R7,A
346      09                 IN A,P1
347      53                 ANL A,#0F
348      0F                 |
349      4F                 ORL A,R7
34A      AF                 MOV R7,A
34B      23                 MOV A,#7D
34C      7D                 |
34D      62                 MOV T,A
34E      FD                 MOV A,R5
34F      39                 OUT P1,A
350      FE                 MOV A,R6
351      3A                 OUT P2,A
352      00                 NOP
353      00                 NOP
354      00                 NOP
```

| ADDRESS | INSTR | | SOURCE | COMMENTS |
|---------|-------|----------|-----------------|----------|
| 355 | 00 | | NOP | |
| 356 | 00 | | NOP | |
| 357 | 00 | | NOP | |
| 358 | 00 | | NOP | |
| 359 | 00 | | NOP | |
| 35A | 00 | | NOP | |
| 35B | 00 | | NOP | |
| 35C | 00 | | NOP | |
| 35D | 00 | | NOP | |
| 35E | 00 | | NOP | |
| 35F | 00 | | NOP | |
| 360 | D5 | DOLEDS: | SEL RB1 | |
| 361 | E9 | | DJNZ R1,DONELEDS | |
| 362 | 98 | | | |
| 363 | F8 | | MOV A,R0 | |
| 364 | 12 | | JB0 BLINK | |
| 365 | 72 | | | |
| 366 | 32 | | JB1 CYCLE | |
| 367 | 80 | | | |
| 368 | 53 | STEADY: | ANL A,#E3 | |
| 369 | E3 | | | |
| 36A | A9 | | MOV R1,A | |
| 36B | 77 | | RR A | |
| 36C | 77 | | RR A | |
| 36D | 77 | | RR A | |
| 36E | 53 | | ANL A,#1C | |
| 36F | 1C | | | |
| 370 | 64 | | JMP SETLED | |
| 371 | 90 | | | |
| 372 | A9 | BLINK: | MOV R1,A | |
| 373 | 77 | | RR A | |
| 374 | 77 | | RR A | |
| 375 | 77 | | RR A | |
| 376 | 53 | | ANL A,#1C | |
| 377 | 1C | | | |
| 378 | D9 | | XRL A,R1 | |
| 379 | 53 | | ANL A,#1C | |
| 37A | 1C | | | |
| 37B | 64 | | JMP SETLED | |
| 37C | 90 | | | |
| 380 | A9 | CYCLE: | MOV R1,A | |
| 381 | E7 | | RL A | |
| 382 | 53 | | ANL A,#18 | |
| 383 | 18 | | | |
| 384 | 96 | | JNZ SETLED | |
| 385 | 90 | | | |
| 386 | 23 | | MOV A,#04 | |
| 387 | 04 | | | |
| 388 | 64 | | JMP SETLED | |
| 389 | 90 | | | |
| 390 | A8 | SETLED: | MOV R0,A | |
| 391 | F9 | | MOV A,R1 | |
| 392 | 53 | | ANL A,#E3 | |
| 393 | E3 | | | |
| 394 | 48 | | ORL A,R0 | |
| 395 | A8 | | MOV R0,A | |
| 396 | B9 | | MOV R1,#0A | |
| 397 | 0A | | | |
| 398 | C5 | DONELEDS: | SEL RB0 | |
| 399 | FD | | MOV A,R5 | |
| 39A | 43 | | ORL A,#E0 | |
| 39B | E0 | | | |
| 39C | AD | | MOV R5,A | |

| ADDRESS | INSTR | | SOURCE | COMMENTS |
|---------|-------|-----------|-------------|----------|
| 39D | FF | | MOV A,R7 | |
| 39E | 67 | | RRC A | |
| 39F | E6 | | JNC DONETICK | |
| 3A0 | 00 | | NOP | |
| 3A1 | 00 | | NOP | |
| 3A2 | 00 | | NOP | |
| 3A3 | 00 | | NOP | |
| 3A4 | D5 | | SEL RB1 | |
| 3A5 | F8 | | MOV A,R0 | |
| 3A6 | C5 | | SEL RB0 | |
| 3A7 | 53 | | ANL A,#1C | |
| 3A8 | 1C | | | |
| 3A9 | E7 | | RL A | |
| 3AA | E7 | | RL A | |
| 3AB | E7 | | RL A | |
| 3AC | DD | | XRL A,R5 | |
| 3AD | AD | | MOV R5,A | |
| 3AE | 00 | | NOP | |
| 3AF | 00 | | NOP | |
| 3B0 | FC | DONETICK: | MOV A,R4 | |
| 3B1 | 93 | | RETR | |

******************* END OF PROGRAM ***********************

SOBERLIZER PROGRAM FLOW CHART

***************************************************************

```
         +---------------+
         |   POWER ON    |
         +---------------+
                 |
         +---------------+
         |  START CLOCK  |
         |  10 MS. TICK  |
         +---------------+
                 |
       +---------------------+
       |SET L.E.D..CYCLING   |
       +---------------------+
                 |
         +-----------------+
         |TURN ON HEATERS  |
         +-----------------+
                 |
       +-------------------------+
       |WAIT 2 MINUTES TO HEAT UP|
       +-------------------------+
                 |
IGNITION  +-----------------------------+
  OFF-----|  WAIT TILL IGNITION ON      |
          |  CYCLE HEATER OFF & ON      |
          +-----------------------------+
                 |
IGNITION  +-----------------------------+
  ON------|SET GREEN L.E.D. FLASHING    |
          +-----------------------------+
                 |
       +--------------------------+
       |WAIT FOR TEMP. OK & STABLE|
       +--------------------------+
                 |
```

SOBERLIZER PROGRAM FLOW CHART
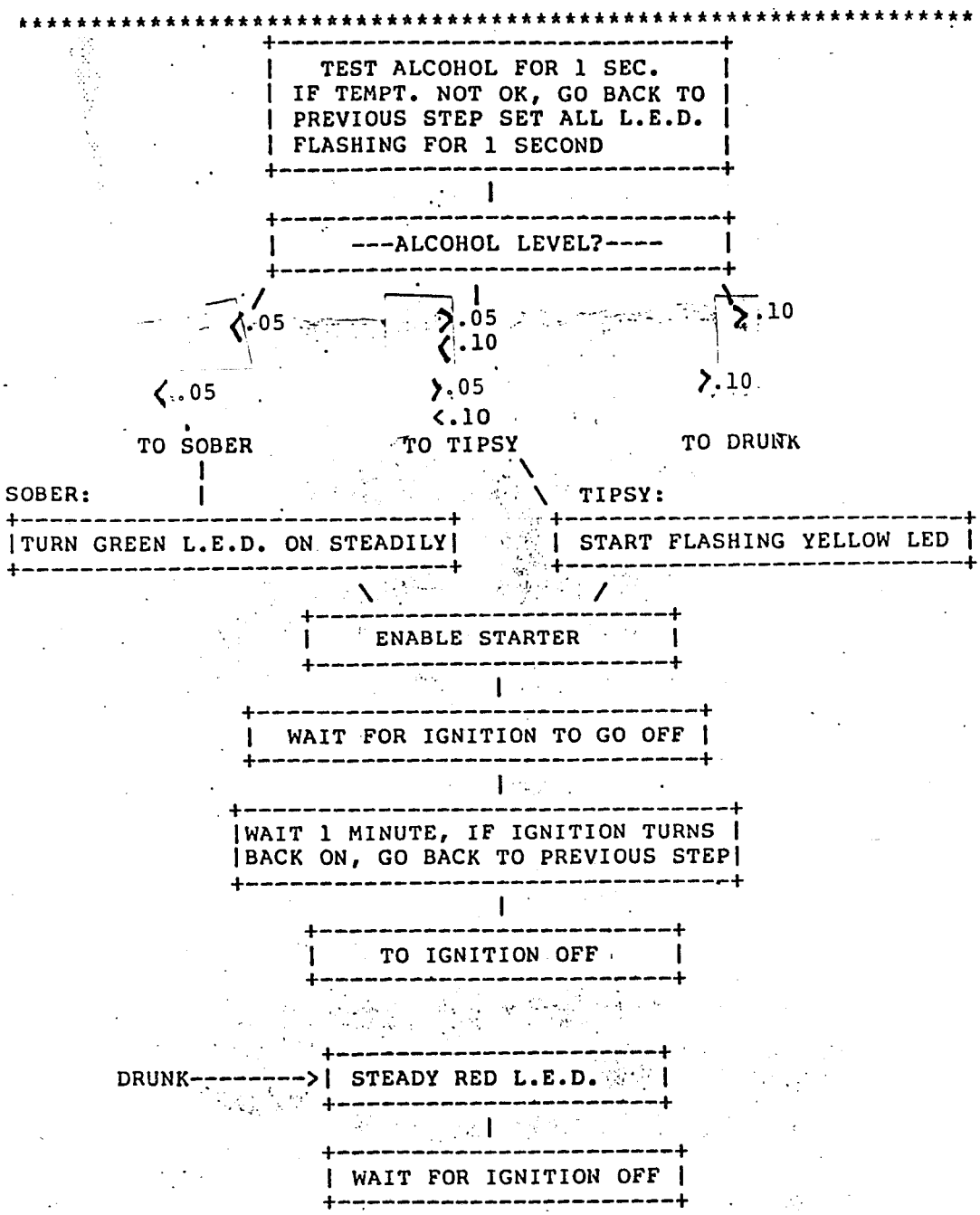

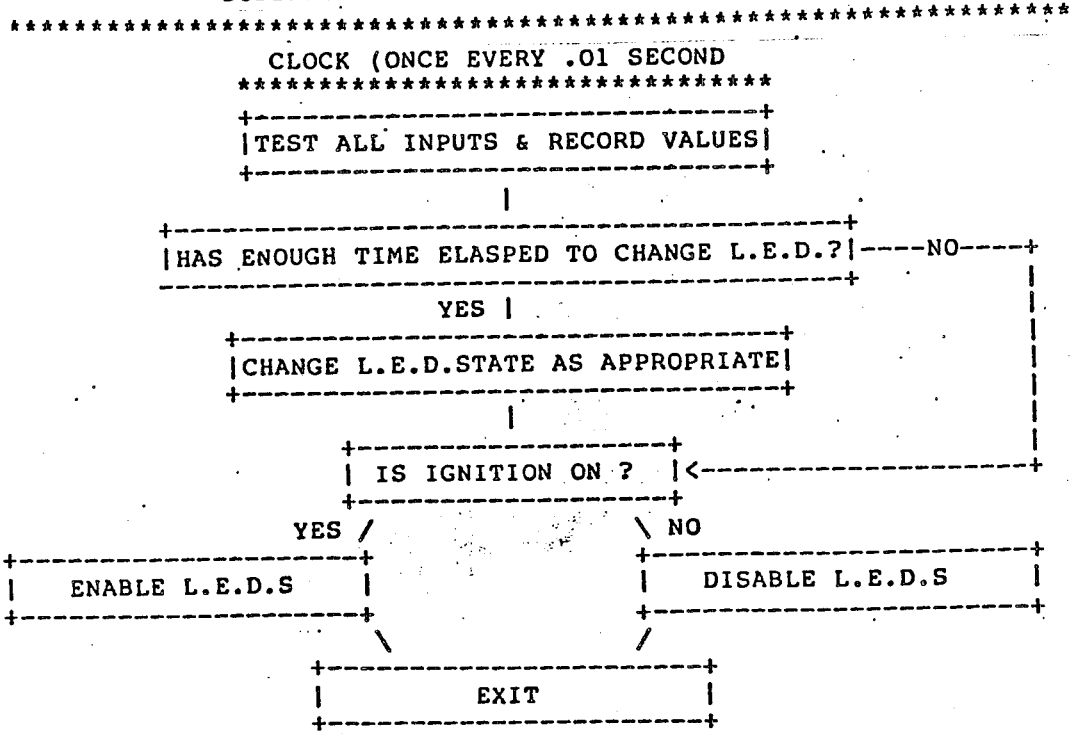

I claim:

1. A sobriety interlock comprising:
   a power supply;
   a ground terminal;
   an "ignition on" input terminal;
   an "OK to drive" output terminal;
   means defining a breath receiving port;
   a thermocouple adjacent to and aligned with said port, said thermocouple being connected to said power supply and said ground terminal and having a junction and a temperature output line for electrical signals generated in response to the temperature of a breath sample flowing through said port, said thermocouple having means for heating the junction thereof to a temperature different from that of a breath sample received in said port;
   a gas sensor adjacent to and aligned with said port, said gas sensor being connected to said power supply and said ground terminal and having an alcohol level output line for electrical signals generated in response to the alcohol level of a breath sample flowing through said port;
   an analog-to-digital converter having a first input connected to the thermocouple output line, a second input connected to the gas sensor output line, and a plurality of output lines for digital signals indicating the temperature and alcohol level of a breath sample flowing through the port;
   a microcomputer responsive to a signal at the "ignition on" terminal to read the digital signals on the converter output lines and to provide a signal at said "OK to Drive" terminal as a function of whether the alcohol level in a breath sample is different from a predetermined level.

2. An interlock as in claim 1 further comprising:
   a clipper circuit connected to said "ignition on" terminal;
   an "ignition enable" circuit connected to said "OK to Drive" line; and
   wherein said clipper circuit is adapted to connected to the key switch in a motorized vehicle, and said "ignition enable" circuit is adapted to be connected between the key switch and the starter solenoid in the vehicle.

3. An interlock as in claim 1 further comprising a heater drive circuit connected between said power supply and said gas sensor, said driver circuit being responsive to a signal from said computer to provide a current to said gas sensor, and wherein said gas sensor has a heating element powered by the heater drive.

4. An interlock as in claim 1 further comprising: a separate indicator connected to each of the plurality of gauge output lines of the computer.

5. An interlock as in claim 1 wherein said analog to digital converter comprises:
   a voltage reference circuit connected between said power supply and said ground terminal and having separate output lines on which said reference circuit provides electrical signals indicative of each of:
     an alcohol high reference;
     an alcohol low reference;
     a breath temperature high reference;
     a breath temperature low reference;
   an alcohol comparator circuit connected to the alcohol sensor output line and having
   a first comparator connected to compare the alcohol sensor output to the alcohol high reference;
   a first alcohol output line to which the first comparator applies a signal indicative of the high comparison result;
   a second comparator connected to compare the alcohol sensor output to the alcohol low reference; and
   a second alcohol output line to which the second comparator applies a signal indicative of the low comparison result;
   a temperature comparator circuit connected to the thermocouple output line and having a third comparator connected to compare the thermocouple output to the temperature high reference;

a fourth comparator connected to compare the thermocouple output to the temperature low reference; and a temperature output line to which said temperature comparator applies a signal indicative of the temperature comparison results.

6. A sobriety interlock as set forth in claim 1, wherein said port defining means comprises a mouthpiece member having a fluid passage therein for receiving a breath sample, said temperature sensor being near the downstream end of said fluid passage.

7. A sobriety interlock as set forth in claim 6, wherein the thermocouple junction is near the downstream end of said fluid passage.

8. A sobriety interlock as set forth in claim 7, wherein the junction of the thermocouple is in the fluid passage at said downstream end thereof.

9. A sobriety interlock as set forth in claim 8, wherein the heating means heats the junction of the thermocouple to a temperature of at least 130° F.

10. A sobriety interlock as set forth in claim 1, wherein said heating means includes a sealed envelope surrounding a portion of the thermocouple, and an electrically actuated heating device within the envelope in heat exchange relationship to the thermocouple.

11. A sobriety interlock as set forth in claim 1, wherein is included a heat insulating tubular member in surrounding relationship to said heating means.

12. A sobriety interlock as set forth in claim 6, wherein is included a tubular extension secured to the mouthpiece and extending outwardly therefrom, said thermocouple extending through at least a portion of said extension, said gas sensor being in said extension downstream of the thermocouple with reference to the direction of flow of a breath sample passing through the extension.

13. A sobriety interlock as set forth in claim 6, wherein is included a housing coupled to the outer end of the extension, said housing containing said converter and said microcomputer, said housing being of a size and weight to permit it to be hand-held as a person blows into the mouthpiece member to deliver a breath sample thereto.

14. A sobriety testing apparatus comprising:
a support;
an elongated, tubular mouthpiece mounted on the support and extending outwardly therefrom, said mouthpiece having a breath-receiving port;
means defining a source of electrical power;
a temperature sensor including a thermocouple carried by the support, said thermocouple having a junction adjacent to and aligned with said port, said temperature sensor being coupled with said power source and having a temperature output line for electrical signals generated thereby as a function of the temperature of a breath sample passing through said port, said thermocouple having means for heating the junction thereof to a temperature higher than that of a breath sample received in said port;
a gas sensor carried by the support adjacent to and aligned with said port, said gas sensor being coupled with said power source and having an alcohol level output line for electrical signals generated thereby as a function of the alcohol level of a breath sample passing through said port;

an analog-to-digital converter having a first input connected to the temperature sensor output line, a second input connected to the gas sensor output line, and a plurality of output lines for digital signals indicating the temperature and alcohol level of a breath sample passing through the port; and a microcomputer responsive to an input signal for reading the digital signals on the converter output lines and to provide an output signal indicative of whether the alcohol level in the breath sample passing through said portion is different from a predetermined level.

15. An interlock as in claim 14, further comprising:
a clipper circuit,
an enable circuit,
said clipper circuit mdapted to be connected to a switch, and said enable circuit is adapted to be connected between the switch and another operable electrical component.

16. Apparatus as in claim 14, further comprising a heater drive circuit connected between said power source and said gas sensor, said driver circuit being responsive to a signal from said computer to provide a current to said gas sensor, and wherein said gas sensor has a heating element powered by the heater drive.

17. Apparatus as in claim 14, further comprising: a separate indicator connected to each of the plurality of gauge output lines of the computer.

18. Apparatus as in claim 14, wherein said analog to digital converter comprises:
a voltage reference circuit connected to said power source and having separate output lines on which said reference circuit provides electrical signals indicative of each of:
an alcohol high reference;
an alcohol low reference;
a breath temperature high reference;
a breath temperature low reference;
an alcohol comparator circuit connected to the alcohol sensor output line and having
a first comparator connected to compare the alcohol sensor output to the alcohol high reference;
a first alcohol output line to which the first comparator applies a signal indicative of the high comparison result;
a second comparator connected to compare the alcohol sensor output to the alcohol low reference; and
a second alcohol output line to which the second comparator applies a signal indicative of the low comparison result;
a temperature comparator circuit connected to the temperature sensor output line and having
a third comparator connected to compare the temperature sensor output to the temperature high reference;
a fourth comparator connected to compare the temperature sensor output to the temperature low reference; and
a temperature output line to which said temperature comparator applies a signal indicative of the temperature comparison results.

19. Apparatus as set forth in claim 14, wherein said mouthpiece has a fluid passage therein for receiving a breath sample, said temperature sensor being near the downstream end of said fluid passage.

20. Apparatus as set forth in claim 19, wherein the thermocouple junction is near the downstream end of said fluid passage.

21. Apparatus as set forth in claim 20, wherein the junction of the thermocouple is in the fluid passage at said downstream end thereof.

22. Apparatus as set forth in claim 21, wherein the heating means heats the thermocouple junction to a temperature of at least 130° F.

23. Apparatus as set forth in claim 14, wherein said heating means includes a sealed envelope surrounding a portion of the thermocouple, and an electrically actuated heating device within the envelope in heat exchange relationship to the thermocouple.

24. Apparatus as set forth in claim 14, wherein is included a heat insulating tubular member in surrounding relationship to said heating means.

25. Apparatus as set forth in claim 19, wherein said support includes a tubular extension secured to the mouthpiece and extending outwardly therefrom, said temperature sensor extending at least a portion of said extension, said gas sensor being in said extension downstream of the temperature sensor with reference to the direction of flow of a breath sample passing through the extension.

26. A sobriety interlock as set forth in claim 19, wherein said support includes a housing coupled to the outer end of the extension, said housing containing said converter and said microcomputer, said housing being of a size and weight to permit it to be hand-held as a person blows into the mouthpiece member to deliver a breath sample thereto.

27. Apparatus as set forth in claim 14, wherein the microprocessor is operable to provide said output signal thereof when the temperature of the thermocouple is in a predetermined temperature range.

* * * * *